United States Patent
Bellar et al.

(10) Patent No.: US 10,675,320 B2
(45) Date of Patent: Jun. 9, 2020

(54) SUPPRESSION OF ANTIMICROBIAL PROTEIN LEVELS

(71) Applicant: University of Louisiana at Lafayette, Lafayette, LA (US)

(72) Inventors: David Bellar, Lafayette, LA (US); Randy Aldret, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 0 days.

(21) Appl. No.: 16/242,095

(22) Filed: Jan. 8, 2019

(65) Prior Publication Data
US 2019/0209635 A1    Jul. 11, 2019

Related U.S. Application Data

(60) Provisional application No. 62/614,522, filed on Jan. 8, 2018.

(51) Int. Cl.

| | |
|---|---|
| A61K 36/00 | (2006.01) |
| A61K 36/45 | (2006.01) |
| A61K 36/74 | (2006.01) |
| A61K 36/28 | (2006.01) |
| A61K 36/71 | (2006.01) |
| A61K 36/07 | (2006.01) |
| A61P 31/00 | (2006.01) |
| A61K 36/8962 | (2006.01) |
| A61K 36/87 | (2006.01) |
| A61K 36/52 | (2006.01) |
| A61K 36/73 | (2006.01) |
| A61K 9/00 | (2006.01) |
| A61K 36/76 | (2006.01) |

(52) U.S. Cl.
CPC .............. *A61K 36/45* (2013.01); *A61K 9/006* (2013.01); *A61K 36/07* (2013.01); *A61K 36/28* (2013.01); *A61K 36/52* (2013.01); *A61K 36/71* (2013.01); *A61K 36/73* (2013.01); *A61K 36/74* (2013.01); *A61K 36/76* (2013.01); *A61K 36/87* (2013.01); *A61K 36/8962* (2013.01); *A61P 31/00* (2018.01)

(58) Field of Classification Search
None
See application file for complete search history.

(56) References Cited

U.S. PATENT DOCUMENTS

2012/0046323 A1*  2/2012  Fought ................... A01N 37/50
514/355

* cited by examiner

*Primary Examiner* — Qiuwen Mi
(74) *Attorney, Agent, or Firm* — Richard L. Vail; Russel O. Primeaux; Kean Miller LLP

(57) ABSTRACT

Exercise is a stressor that is known to in some cases suppress antimicrobial protein levels, particularly secretory immunoglobulin type A (IgA). Athletes in the midst of in-season training often demonstrate low levels of sIgA and supplements may enhance post exercise mucosal immune function. A study was conducted where three treatments were administered (botanical spray, botanical drops, placebo) at the onset of 30 minutes of 80% V02 max cycle ergometer exercise. Secretory IgA and Human Alpha Defensin were quantified in saliva samples 30 minutes and 90 minutes post exercise. Analysis revealed a significant treatment effect at 30 min (p=0.030) with post hoc testing revealing a difference between the botanical spray and placebo (p=0.027), but by 90 minutes there was no differences by treatment (p=0.758). Based upon this study, it appears that a single dose of the tested botanical can provide enhanced mucosal immune capability for a short time post exercise.

5 Claims, No Drawings

SUPPRESSION OF ANTIMICROBIAL PROTEIN LEVELS

CROSS REFERENCE TO RELATED APPLICATION

This application claims priority to a U.S. Provisional Application No. 62/614,522 titled "SUPPRESSION OF ANTIMICROBIAL PROTEIN LEVELS" filed on Jan. 9, 2018.

STATEMENT REGARDING FEDERALLY SPONSORED RESEARCH OR DEVELOPMENT

Not applicable.

REFERENCE TO A "SEQUENCE LISTING", A TABLE, OR COMPUTER PROGRAM

Table 1 provides a statistics analysis describing physical characteristics of participates of the study.

Table 2 presents the measure concentration of salivary IgA before and after exercise.

Table 3 presents an analysis of variance for measurements corrected for osmolality.

Table 4 presents an analysis of variance for measurements controlled for changes in total protein.

Table 5 presents an analysis for measurement controlled for changes in salivary flow rate.

Table 6 presents an analysis of variance for salivary alpha amylase activity.

Table 7 presents an analysis of variance for proline rich protein concentration.

FIELD OF THE INVENTION

The present invention relates to the general field of kinesiology, especially as it relates to prevention of illness in athletes. The invention relates generally to a system and method of administrating botanicals. In particular, the invention relates to administration of Biocidin®.

BACKGROUND OF THE INVENTION

Exercise is a known stressor that has influence over many different physiological systems in the body. There is evidence in the literature that long-term training in athletes can negatively affect antimicrobial protein levels in the oral cavity. Furthermore it has been reported that athletes face a higher incidence of upper respiratory tract infection (URTI) compared to more sedentary individuals. Based upon the reports in the literature, it is understood that long-term training for sport performance is a stressor that can both elevate physiological potential for in the athletic arena, but may depress function in other system. Moreira et al. reported that a 2-week detraining period after a competitive soccer season attenuated Immunoglobulin A (sIgA) suppression and symptomology of URTI due to training. From this study it can be suggested that mucosal immunity can quickly rebound if rest and recovery are allowed for athletic populations. However, the demands placed upon athletes, reduced mucosal immunity and risk for URTI are likely to remain an issue into the future.

It has also been determined by previous research that certain forms of acute athletic performance and exercise have the ability to suppress immunoglobulin secretion in the oral cavity. However, most of these exercises are long duration and aerobic, the evidence for the changes in antimicrobial protein with short-term intermittent exercise is less clear with some evidence suggesting no change in immunoglobulin type A. Additionally, Li and Gleeson reported that 60% maximum aerobic capacity (V02 max) cycling for 2 hours did not negatively impact sIgA secretion rates. However, MacKinnon and Jenkins had previously reported a decline in sIgA with intense interval exercise (0.075 g*kg$^{-1}$) on a cycle ergometer. Though there is much study yet needed to fully elucidate the responses of antimicrobial proteins in the saliva with all forms of exercise there is enough evidence that further study is warranted particularly regarding methods to increase antimicrobial protein levels.

Some botanicals, such as baker's yeast beta glucan, have been shown to increase sIgA in saliva and help decrease symptoms of cold and flu post exercise. Shiitake mushrooms are another natural food substance that is known to contain beta glucans, which may be beneficial for human health. Shiitake mushrooms have been demonstrated to have antioxidant activity post exercise, but no evidence currently exists to examine changes in oral anti-microbial protein levels post exercise. Therefore, the purpose of the initial investigation was to examine the effects of a botanical supplement on secretory immunoglobulin A and alpha defensing levels post-exercise.

DETAILED DESCRIPTION OF THE INVENTION

A series of studies were conducted to evaluate the effectiveness of Biocidin®. Biocidin® is comprised of Bilberry extract (25% anthocyanosides), Noni, Milk Thistle, Echinacea (purpurea & angustifolia), Goldenseal, Shiitake, White Willow (bark), Garlic, Grapeseed extract (min. 90% polyphenols), Black Walnut (hull and leaf), Raspberry, Fumitory, Gentian, Tea Tree oil, Galbanum oil, Lavender oil (plant & flower), and Oregano oil (plant & flower). For the study 20 apparently healthy male subjects were recruited to participate. Measurements and an associated statistics analysis describing participates is presented in Table 1. On the first visit the subjects gave informed consent after being briefed on the study procedures and then had basic anthropometric information collected (height, weight, body fat percentage determined via 3 site skinfold analysis). The subjects also practiced providing a passive drool sample according to the methods laid out in the Standard Operating Procedures for the Human Performance Lab at the University of Louisiana at Lafayette. Following this assessment the subjects had a tests of maximum aerobic capacity (VO2 max) administered on a cycle ergometer with inspired gases monitored with a CosMed Cardio Pulmonary Exercise Test. In brief, this test consisted of pedaling at a cadence of 60-80 rpm on an electronically braked "bicycle" on which the workload was increased every 2 minutes until the participate voluntarily stops exercising or their oxygen consumption has ceased increasing as determined by computer data assessed in real time. This test concluded the activities of the first lab visit.

The next 2 lab visits were conducted in the morning. The participants reported to the lab in an overnight fasted state without having brushed their teeth. The exercise for these visits involved a 30 minute cycling protocol at 70% of the maximum workload (in watts) achieved during the test of maximum aerobic capacity. The participants provided a baseline, 30 min and 90 min post exercise saliva samples (2 ml total volume per collection, 5 minute timed collection) into pre-weighted cryovials. Prior to each exercise session the participants received one of two treatments in a random order. The treatments consist of saline solution to be sprayed in the oral cavity (small manual squirt bottle), or Biocidin solution in a spray bottle. The participants received a second dose immediately after exercise and after the 30 minute saliva sample were collected.

After collection the saliva samples were frozen at −35 degree Celsius in a dedicated freezer in a secure laboratory with limited access. Prior to analysis the saliva samples was allowed to come to room temperature and centrifuged at 1500 g for 15 minutes.

Saliva samples were tested for osmolality via a vapor pressure osmometer (EliTech VAPRO). The instrument has a measurement range of 20 to 3200 mmol*kg and requires 10 pg of samples. The Osmometer was calibrated prior to testing using a three point linear calibration. The saliva samples were tested immediately after collection, prior to being frozen for storage.

Saliva samples were tested for total protein content after thawing. The analysis was conducted on a Qubit 3.0 Fluorometer using a standard total protein assay kit. (Fisher Scientific, Qubit Protein Assay kit). The assay kit has a range of 12.5 pg/ml to 5 mg/ml with 1iAL to 204 of sample.

After collection, saliva samples were weighted on an analytic balance (Ohaus, Model PA313) to determine the salivary flow rates. These final weights were subtracted from the weight of the vial. A density of 1.0 g/ml was assumed and the final weights were divided by 5 min. (time of collection) to arrive at ml/min secretion rate.

Thawed saliva samples were analyze for salivary alpha amylase activity (SAA) using a commercial calorimetric assay (Salimetrics, Inc). The assay involves the detection of 2-chloro-p-nitrophenol separated from maltotriose which can be detected at 405 nm. The assay was conducted in standard microplates and read with a kinetic microplate reader (BioTek ELx 808uv).

Thawed saliva samples were analyzed for Salivary Immunoglobulin A in duplicate using a commercial sandwich ELISA (Eagle Biosciences). The absorbance was read at 450 nm with a reference filter at 690 nm.

Salivary Praline Rich Protein and Bacterial Permeability Increasing Protein biomarkers were analyzed using sandwich ELISA kits (Cloud-Clone Corp.). Analysis was conducted in duplicate and read at 450 nm.

Changes in biomarkers by treatment (Biocidin® vs Placebo) by time (pre, post 30, post 90) were assessed via Repeated Measures analysis of variance (ANOVA). Post Hoc Analysis was carried out via paired samples t-tests for all significant interaction effects, All statistical procedures were carried out using a modern statistical software package OMP 12.0 Pro). Statistical significance was set a priori at alpha <0.05.

With relatively few exceptions Bacterial Permeability increasing Protein (BPI) was not detected in the saliva collected with ELISA, and therefore could not be statistically analyzed. The assay kit has a limit of detection of 31 pg/ml, which is sufficient to detect BPI in the concentrations listed in some publications. However, the actual normal concentrations of BRI in human saliva are not well characterized. Until a greater understanding of the normal concentrations of BPI in saliva can be developed including any other potential confounders (such as diurnal effects) this biomarker should not be included in further studies.

Salivary IgA data was examined in 4 different manners: 1) measured concentration (see Table 2), 2) controlled for changes in Osmolality (see Table 3), 3) controlled for changes in total protein (see Table 4) and 4) controlled for changes in Salivary Flow Rate (see Table 5). Repeated measures ANOVA for concentrations (raw) did not reveal a main effect for treatment (F=0.008, p=0.929) nor a significant effect for treatment by time (F=1.03, p=0.653)

As presented in Table 3, repeated measures ANOVA for concentrations (controlled for Osmolality) did not reveal a main effect for treatment (F=0.233, p=0.636) nor a significant effect for treatment by time (F=0.561, p=0.607)

As presented in Table 4, repeated measures ANOVA for concentrations (controlled for total protein) did not reveal a main effect for treatment (F=0.118, p=0.733) but did reveal a significant effect for treatment by time (F=2.60, p=0.044). Post hoc testing did reveal a significant different at the 90 minute post exercise time point (p=0.05).

As presented in Table 5, repeated measures ANOVA for concentrations (controlled for salivary flow rate) did not reveal a main effect for treatment (F=0.020, p=0.889) nor a significant effect for treatment by time (F=2.05, p=0.071)

As presented in Table 6, repeated measures ANOVA for Salivary Alpha Amylase activity did not reveal a main effect for treatment (F=0.007, p=0.934) nor a significant effect for treatment by time (F=0.315, p=0.731)

As presented in Table 7, repeated measures ANOVA for Proline Rich Protein (PRP) concentrations did not reveal a main effect for treatment (F=0.0452, p=0.832) nor a significant effect for treatment by time (F=0.901, p=0.419)

The results of the present study do lend additional support to the efficacy of Biocidin® spray for post exercise mucosal immunity support. While biomarkers such as SAA, PRP and BPI were not increased with Biocidin®, the change noted for sIgA is highly relevant as this is the most abundant antimicrobial protein (AMP) present in saliva. It is also important to note that controlling the analysis of sIgA for total protein content has been previously reported on in the literature in response to exercise stress (MacKinnon and Jenkins, 1993). More commonly studies control sIgA for salivary flow rate through the extrapolation of a secretion rate (Akimoto, 2003). It should be noted that while non-significant a trend in the data for sIgA secretion rate that was similar to the finding for sIgA/total protein was noted. These parallel data lend support to the conclusion that Biocidin® is indeed effective for augmenting sIgA post exercise.

The lack of findings from the BPI and PRP may be due to the lack of available data regarding the response of these AMPS to exercise. It is possible that these are not responsive to exercise stimuli. Salivary Alpha Amylase was notably lower during the pre-exercise time, a finding that has been previously reported (Walsh et al., 1999) and is likely due to anticipatory psychological stress. This biomarker is also know to increase post exercise, which was noted in the results of the present study. However, nutritional supplements that are effective at augmenting sIga such as beta glucan (McFarlin et al., 2013), have not been investigated with Salivary alpha amylase. Given the responsiveness of salivary alpha amylase to sympathetic tone (Messina et al. 2016) the pre exercise anticipatory phase and increased sympathetic activity during exercise may mask other potential changes in activity level.

TABLE 1

| Participants (M ± SD) | |
| --- | --- |
| Height (cm) | 176.4 ± 4.7 |
| Weight (kg) | 82.8 ± 13.3 |

TABLE 1-continued

| Participants (M ± SD) | |
|---|---|
| Body Fat (%) | 14.7 ± 4.3 |
| VO2 max (ml/kg*min) | 27.4 ± 4.8 |

TABLE 2

| Treatment (M ± SD) | Pre Exercise | 30 min Post Ex | 90 min Post Ex |
|---|---|---|---|
| Biocidin (μg/ml) | 296.9 ± 347.6 | 246.0 ± 261.4 | 294.8 ± 394.4 |
| Placebo (μg/ml) | 279.1 ± 276.9 | 305.9 ± 362.7 | 276.7 ± 405.9 |

TABLE 3

| Treatment (M ± SD) | Pre Exercise | 30 min Post Ex | 90 min Post Ex |
|---|---|---|---|
| Biocidin (pg/ml*mOSM/kg$^{-1}$) | 4.85 ± 5.98 | 4.27 ± 5.06 | 4.77 ± 6.62 |
| Placebo (μg/ml*mOSM/kg$^{-1}$) | 4.71 ± 5.15 | 5.93 ± 8.12 | 5.89 ± 9.22 |

TABLE 4

| Treatment (M ± SD) | Pre Exercise | 30 min Post Ex | 90 min Post Ex |
|---|---|---|---|
| Biocidin (μg/ml*ng protein$^{-1}$) | .886 ± 1.31 | .630 ± .703 | .928 ± 1.31* |
| Placebo (μg/ml*pg protein$^{-1}$) | .737 ± .704 | .778 ± .902 | .667 ± .868 |

*denotes significantly different than placebo

TABLE 5

| Treatment (M ± SD) | Pre Exercise | 30 min Post Ex | 90 min Post Ex |
|---|---|---|---|
| Biocidin (ig/min) | 61.8 ± 97.6 | 38.8 ± 53.1 | 65.9 ± 94.24 |
| Placebo (μg/min) | 54.6 ± 63.67 | 62.4 ± 63.2 | 57.7 ± 93.2 |

TABLE 6

| Treatment (M ± SD) | Pre Exercise | 30 min Post Ex | 90 min Post Ex |
|---|---|---|---|
| Biocidin U/ml | 34.3 ± 32.4 | 63.1 ± 128.5 | 37.8 ± 41.45 |
| Placebo U/ml | 39.7 ± 48.7 | 51.2 ± 57.1 | 45.6 ± 58.5 |

TABLE 7

| Treatment (M ± SD) | Pre Exercise | 30 min Post Ex | 90 min Post Ex |
|---|---|---|---|
| Biocidin (ng/ml) | 842.2 ± 1313.6 | 1095.92 ± 1719.9 | 951.65 ± 1448.7 |
| Placebo (ng/ml) | 1108.5 ± 1517.8 | 856.52 ± 1388.7 | 1279.61 ± 1671.9 |

We claim:

1. A method for suppressing upper respiratory tract infection comprising:
    (a) administrating a dose of a botanical,
    (b) wherein the botanical is comprised of Bilberry extract, Noni, Milk Thistle, Echinacea, Goldenseal, Shiitake, White Willow bark, Garlic, Grapeseed extract, Walnut hull and leaf, Raspberry, Fumitory, Gentian, Tea Tree oil, Galbanum oil, Lavender oil, and Oregano oil.

2. The method of claim 1, wherein the dose of botanical is administered prior to exercise.

3. The method of claim 1, wherein the dose of botanical is administered during exercise.

4. The method of claim 1, wherein the dose of botanical is administered after exercise.

5. The method of claim 1, wherein the dose of botanical is administered by spraying in the oral cavity.

* * * * *